United States Patent [19]

Rey et al.

[11] 4,225,979
[45] Oct. 7, 1980

[54] TOTAL OR PARTIAL URETERAL PROSTHESIS

[76] Inventors: Pierre Rey, 18 rue Aristide Briand, 77400 Thorigny; Jacqueline Leandri, 50 Avenue de Clichy, 75018 Paris; Clément Abbou, 43 Av. de la Dame Blanche, 94120 Fontenay Sous Bois, all of France

[21] Appl. No.: 964,433

[22] Filed: Nov. 28, 1978

[30] Foreign Application Priority Data

Nov. 28, 1977 [FR] France .................................. 77 35685

[51] Int. Cl.³ ........................... A61F 1/24; A61F 1/00; A61M 27/00
[52] U.S. Cl. ........................................ 3/1; 128/350 V
[58] Field of Search ............ 3/1, 1.4; 128/350, 350 V, 128/348, 334 R

[56] References Cited

U.S. PATENT DOCUMENTS

| 3,783,454 | 1/1974 | Sausse et al. | 3/1 |
| 3,881,199 | 5/1975 | Treace | 128/350 R X |

FOREIGN PATENT DOCUMENTS

| 2714810 | 10/1977 | Fed. Rep. of Germany | 3/1 |
| 2116838 | 7/1972 | France | 3/1 |

OTHER PUBLICATIONS

"Total Replacement of Ureter by a Scurasil Prosthesis in Pigs", by J. C. Djurhuus et al., British Journal of Urology, (1974), 46, pp. 415-424.

Primary Examiner—Ronald L. Frinks

[57] ABSTRACT

A ureteral prosthesis comprises a generally tubular member (9) of a urine-resistant and physiologically acceptable flexible material. The tubular member (9) has at least one permanent distortion (7) along its length, and has at least one anti-reflux valve (5) at its downstream end. The permanent distortion (7) is formed so that it co-operates with valve (5) in use of the prosthesis so as to vary the internal volume of the aforesaid prosthesis under the influence of physiological movement of a body part of a patient in which the prosthesis is implanted, which movement results in deformation of the flexible tubular member (9), whereby a pump-action is obtained in the prosthesis.

20 Claims, 15 Drawing Figures

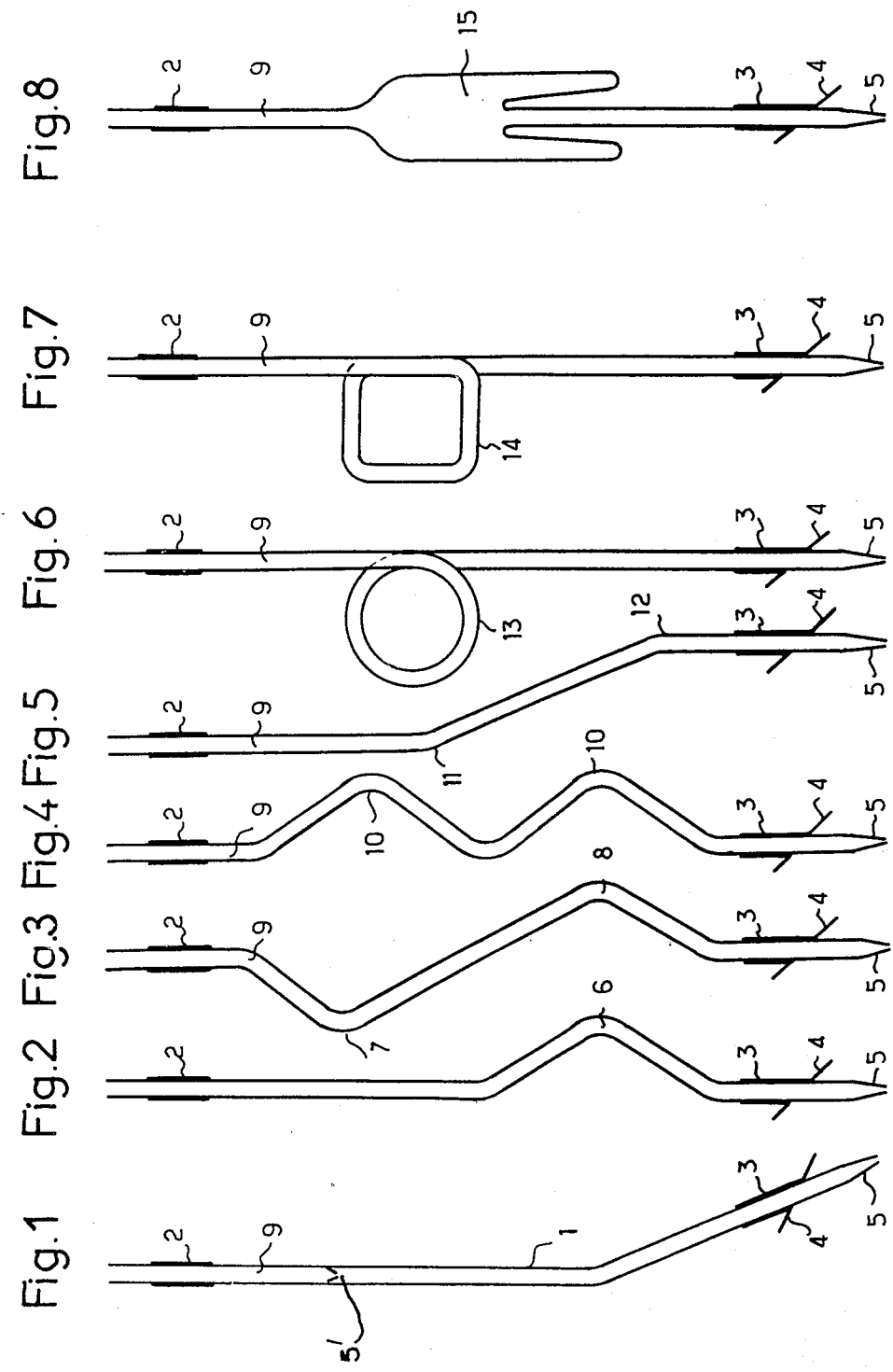

TOTAL OR PARTIAL URETERAL PROSTHESIS

BACKGROUND OF INVENTION

The present invention relates to a total or partial ureteral prosthesis. Known ureteral prostheses suffer from various difficulties and complications in their use. The difficulties encountered include the following: the need to adapt the prosthesis to the patient's size involves risks of distortion and consequent stasis, and risks of migration of the prosthesis; positioning of existing ureteral prostheses frequently causes residual hydronephroses, which are the result of persistent stasis; the positioning of existing ureteral prostheses also frequently involves urinary infections and lithiases which can complicate these infections.

The difficulties encountered are due to several factors and particularly to the more or less substantial rigidity of the prosthesis, to its shape, to the cross-section of its aperture, the quality of its internal surface and to the presence or absence of an anti-reflux system.

Known ureteral prostheses which attempt to solve the above difficulties include "straight" prostheses made of "Scurasil" (French Trade mark registered by RHONE POULENC, designating a dimethylpolysiloxane), and including muffs made of "Rhodergon" (Registered French Trademark), a velvet cloth of polyester (see Sausse et al, U.S.P at. No. 3,783,454, col. 2, lines 44–51) to anastomose the prosthesis to the surrounding tissue.

Although there is a description in existence of these straight ureteral prostheses made of "Scurasil" which states that they are made with an anti-reflux valve at their vesical extremity (cf.BRITISH JOURNAL OF UROLOGY (1974) 46,415–424), nevertheless the straight ureteral prostheses made of "Scurasil" and perfected by RHONE POULENC from 1967 onwards are not provided with anti-reflux valves, due to the need to provide for an internal surface of high quality which led the RHONE POULENC Company to perfect a process of lacquering the internal side walls of the prostheses as well as the external ones—at least partially—with the aid of a vulcanized silicone elastomer smooth coating. Since, however, this lacquering process is very difficult to apply to anti-reflux valves, it has not been found practical to produce such prostheses as proposed in conformity with the foregoing publication, which have both a high quality internal surface which is obtained by lacquering and an anti-reflux valve.

This is made particularly clear in the literature distributed by the RHONE POULENC Company concerning its "Scurasil" ureteral-vesical prostheses.

Since the above ureteral prosthesis is of a kind which does not solve the above problems in their entirety, by reason of its insufficient flexibility or of its nonextensibility, another ureteral prosthesis has also been proposed by the same Company, which prosthesis, also made of "Scurasil", is made up of a flexible, extensible helical tube which is, therefore, of variable length according to the size which it is wished to give to the prosthesis. Such a prosthesis also solves the problem of adaptation of the prosthesis to the size of the patient, as well as the problem of distortion.

However, these helical prostheses; like "straight" ureteral prostheses, do not include any anti-reflux valve and do not have a peristaltic mechanism. The absence of a peristaltic mechanism from the prostheses constitutes an obstacle to the outflow of urine, so that these prostheses are also unable to solve all the difficulties mentioned above.

Although the ureteral prostheses which have just been described are clearly superior to the ureteral prostheses which were proposed still earlier (which comprised essentially rigid tubes or reinforced tubes) they do have an undesirable resistance to outflow which results in their being unable to prevent the risks of consequential stasis as well as urinary infections and lithiases.

In the above-mentioned publication it was also proposed, in order to ensure a suitable peristaltic mechanism favoring the outflow of urine, to position a centrifugal pump between the kidney and the bladder, the aforesaid pump being driven by a direct current electric motor, the intermittent operation of which would be controlled by an impulse generator.

Although such a centrifugal pump system provides the desired peristaltic mechanism, nevertheless the implantation of the pump and of the associated electrical and electronic systems for controlling it, present numerous disadvantages. Numbered among these must be the complication of surgical intervention for the purposes of implantation, the relatively unsatisfactory compatibility of the equipment and the formation of encrustations (notably crystallized mineral salts) which produce lithiases, so that the implantation of these pumps has not been developed because their disadvantages outweigh their advantages.

It has also been proposed to assist the outflow of urine in ureteral prostheses with the aid of a tubular diaphragm pump which is inserted into the ureteral prosthesis and which is associated with a hydraulic system implanted in a pleural cul-de-sac and which controls displacement of the aforesaid pump under the influence of the respiratory movement of the patient.

This system is however of great complexity and is difficult to construct as well as being difficult to implant because of the complications of the necessary surgical intervention required for implantation and the consequences arising from such an implantation, so that this system has not been retained in practice for the purposes of solving the difficulties posed by ureteral prosthesis.

SUMMARY OF INVENTION

It is an object of the present invention to provide an improved total or partial ureteral prosthesis which better meets the requirements of medical practice than do the known ureteral prostheses proposed according to the above-mentioned publication, and in particular which minimizes the above-mentioned difficulties brought about by known prostheses, by means of its good compatability with the surrounding body tissue, in use thereof, its adaptability to the size of the patient, its flexibility which allows it to overcome distortion problems, and its construction which provides the desired pump action in order to assist the outflow or urine, which allows its implantation with the use of only simple surgical techniques and which does not require any large and/or complicated control mechanism.

The present invention provides a total or partial ureteral prosthesis comprising a generally tubular member of a urine-resistant and physiologically acceptable flexible material which tubular member has at least one permanent distortion along its length, and has at least one anti-reflux valve at its downstream end, such permanent distortion being formed so that it co-operates with the valve in use of the prosthesis so as to vary the internal volume of the aforesaid prosthesis under the influence of a physiological movement of a patient in which the prosthesis is implanted, which movement results in deformation of the flexible tubular member, whereby a pump-action is obtained in the prosthesis.

In the prosthesis of the invention the valve co-operates with the above-mentioned permanent distortion in order to vary the internal volume of the tubular member of the prosthesis under the action of physiological movements of various parts of the patient's body to thereby provide the desired pump action.

The permanent distortion can be in the form of at least one elbow forming an angle, usually of less than 90°, relative to the principal longitudinal axis of the tubular member which is the general direction of implantation of the prosthesis. The distortion can, with advantage, be in the shape of at least one "V" and where two or more "V" shapes are included these can be arranged either side by side or on opposite sides of the longitudinal axis of the prosthesis. The permanent distortion conferred on the ureteral prosthesis in conformity with the invention can also be in the form of a circular loop or an appropriate polygonal shape with rounded angles. The permanent distortion can also be in the form of a diaphragm of the Bellofram type, or any other shape which can, in association with the anti-reflux valve, provide the required pump action.

Preferably a second anti-reflux valve is provided in the tubular member upstream of the permanent distortion. In general, the upstream end of the prosthesis which is implanted within the ureteral stump in use of the prosthesis is preferably formed so as to allow an outflow of urine even when the upstream end of the tube accidentally abuts an obstacle, such as a wall of body tissue, which could then occlude the upstream end of a tubular member not so formed.

The invention relates most particularly to partial or total ureteral prostheses which are in conformity with the foregoing stipulations, as well as the means which are proper to their manufacture and the prosthetic assemblies in which such prostheses are included.

BRIEF DESCRIPTION OF DRAWING

The above and further preferred features of the invention appear from the following description, by way of example, of some preferred embodiments illustrated with reference to the accompanying drawings in which:

FIGS. 1 to 8 represent sectional views along their longitudinal axes, of eight different embodiments of an ureteral prosthesis according to the present invention.

Figure 9:
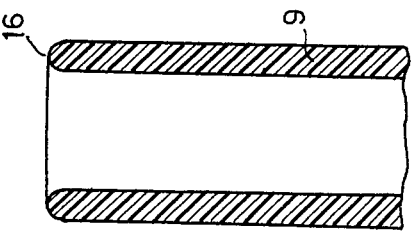
FIGS. 9 to 15 show, on an enlarged scale in partial longitudinal section, different forms of the upstream end of a said ureteral prosthesis which end is intended to be implanted within the ureteral stump or within the pelvis of the kidney.

However, it should be clearly understood that these drawings and the relevant descriptive sections are given solely by way of illustration of the subject of the invention and do not in any way constitute a limitation thereof.

DETAILED DESCRIPTION OF EMBODIMENTS

Referring to each of FIGS. 1 to 8, a total or partial ureteral prosthesis of the invention comprises a generally tubular member 9 having a permanent distortion and, in the region of each of its upstream and downstream ends, is provided a ring 2, 3 made of appropriate re-inhabitable material, e.g. a cloth material which promotes the ingrowth of tissue. In addition, the prosthesis is provided, in known manner, with a flange 4 made of an appropriate tissue ingrowth material, in the neighbourhood of the downstream or vesical end, to allow the prosthesis to be readily anastomosed to the bladder, the aforesaid flange being disposable either parallel to the general longitudinal axis of the prosthesis or obliquely relative to said axis.

The ureteral prosthesis is also fitted with an anti-reflux valve 5 which in the case of the embodiments illustrated is disposed at the downstream end of the prosthesis. A second anti-reflux valve 5' may be provided upstream of the permanent distortion.

The permanent distortion in the tubular member of the ureteral prosthesis can take various forms, as shown in FIGS. 1 to 8, including the following forms:

an elbow shape, 1 shown in FIG. 1;

a "V" shape 6, shown in FIG. 2;

a "Z" shape made up of two linked "V" shapes, 7 and 8, disposed on either side of the general longitudinal axis of the tubular member 9, shown in FIG. 3;

a "W" shape 10, shown in FIG. 4;

two adjacent elbows, 11 and 12, shown in FIG. 5;

a circular loop 13, shown in FIG. 6 or some other structure turned around substantially back on itself 14, as shown in FIG. 7; or a Bellofram type diaphragm 15, as shown in FIG. 8; or indeed any other equivalent distortion capable of providing, in association with the anti-reflux valve 5, pump-like action.

The combination of the permanent distortion with the anti-reflux valve enables the prostheses of the invention to provide a pump-action by means of the variation in the volume of the prosthesis under the influence of the natural physiological movement of the organism in which the prosthesis is implanted, particularly under the influence of respiratory movement, lateral movement of the body relative to the spinal column during ambulation and, if appropriate, movement of the abdominal viscera.

Ureteral prostheses according to this present invention preferably include, in addition, at their upstream end which end is, in use, implanted within the ureteral stump, or within the calyx or pelvis of the kidney—an improvement comprising the upstream end being formed so as to allow a normal outflow of urine into the ureteral prosthesis, even where the upstream end of the tubular member happens to abut an obstacle and in particular against a wall of body tissue, for example, against the side wall of the pelvis of the kidney. Advantageously also the upstream end of the tubular member 9 of the ureteral prosthesis is formed with rounded edges 16 to minimize the possibility of any injury to surrounding tissues.

More advantageously still, the upstream end of the tubular prosthesis 7 is formed so as to allow an outflow of urine, even when such upstream end is crushed against an obstacle such as a wall of body tissue. Several examples of particularly preferred constructions are shown in FIGS. 10 to 15.

Figure 10:
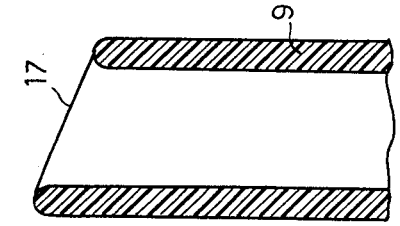
Figure 11:
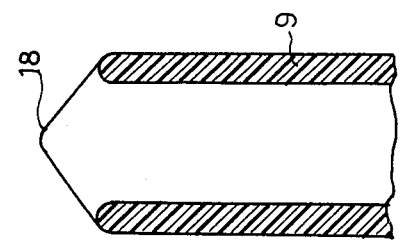
Figure 12:
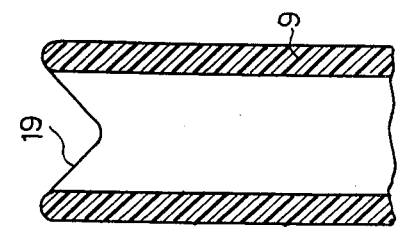
Figure 13:
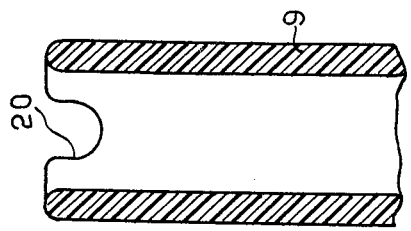

Thus the upstream end of the tubular member 9 may be bevelled 17 as in FIG. 10, in the form of a cone or wedge 18 as in FIG. 11 or provided in the end wall with an angular recess 19 as in FIG. 12, a slot 20 as in FIG.

Figure 14:
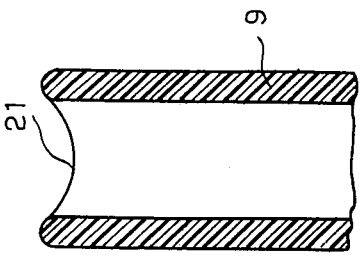

13, or a basin-shaped recess 21 as in FIG. 14. Other similar forms of construction are also possible.

Figure 15:
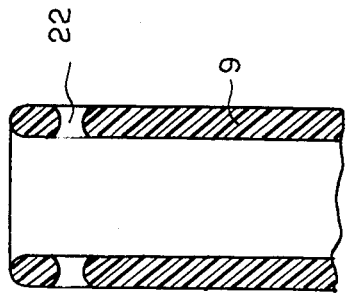

In addition it is possible to provide the tubular member 9 in the neighbourhood of its upstream end, with at least one orifice 22 in the side wall as shown in FIG. 15 in order to allow a continued outflow of urine into tubular member 9 even in the event of crushing of the upstream end 16 of the tubular member against body tissue. Where more than one orifice is provided, these can of course be disposed in various relative arrangements.

Advantageously the edges of the upstream end of the tubular member in each of the embodiments of FIGS. 10 to 15 are provided with rounded edges as in FIG. 9, in order to avoid any trauma to the surrounding body tissue.

Total or partial ureteral prostheses in conformity with the invention are manufactured of any urine resistant physiologically acceptable flexible material, and preferably of a flexible plastic material, such as for example silicone, polyurethane or some other analogous material and desirably provided with a "perfect" surface at least on an internal surface.

This "perfect" surface is conferred on it at the time of its manufacture by any appropriate process, for example by the process which is the subject of the Patent AGENCE NATIONALE DE VALORISATION DE LA RECHERCHE—ANVAR No.77 07091, or by the process which is the subject of the RHONE POULENC Patent No. 71 04613.

The permanent distortion may be introduced into the tubular member of the total or partial ureteral prostheses according to this present invention, in the course of their manufacture, by one of the above-mentioned processes or by any other appropriate process.

Contrary to the statements of manufacturers of known ureteral prostheses which do not have antireflux valves and which are not provided with any "Peristaltic mechanism", which statements tend to claim that the pelvis of the kidney and the ureteral stump subjacent to the prosthesis are emptied in a physiological manner without the necessity for providing any pumping mechanism in the prosthesis by the provision of, for example, an anti-reflux valve, the experiments effected by the above-mentioned Article make it clear that the absence of any "pumping action" or "Peristaltic mechanism" from prosthesis according to said Article constitutes a serious obstacle to the proper outflow of urine and, as a consequence, are conducive to the incidence of infections and stasis.

In contrast, the particular construction of the ureteral prostheses according to the present invention, which do include an anti-reflux valve, which is known per se, arranged at the downstream end of the tubular member in co-operative association with a permanent distortion of the tubular member providing variations in the volume of the aforesaid prostheses resulting from physiological movements of various parts of the patient's body, result in a pump action which in turn facilitates a normal outflow of urine through the aforesaid prostheses.

The new ureteral prostheses according to the present invention provide, in addition to the pump action, other important advantages. In particular their flexibility allows easy adaptation of the prosthesis to the size of the patient. In addition, the particular construction of prostheses conforming to the invention, allows the use of a small cross-sectional diameter—for example less than 3 mm. This has the results of increasing the linear flow speed of the urine and facilitating anastomosis onto small bore urethras.

As is clear from the foregoing, the invention is in no way limited to those advantages of its method of manufacture and of application which has just been described in a more explicit manner. On the contrary, it embraces all variants of them which may occur to the mind of technicians in the matter, without departing from the scope of the present invention as defined in the following claims.

We claim:

1. Total or partial ureteral prosthesis for an organism characterized in that it comprises a generally tubular device with pump effect having an upstream end and a vesical end, compatible with urine and with the organism, made from flexible plastic material which is compatible with the surrounding tissues, which device presents a permanent set distortion on at least one point of its course which modifies the aforesaid course, and is provided with an anti-reflux valve at least on its vesical end, which valve cooperates with the aforesaid set distortion to vary the volume of the aforesaid prosthesis under the action of the physiological movements of the organism, thus creating the desired pump effect.

2. Ureteral prosthesis according to claim 1, characterized in that said permanent set distortion confers an elbowed shape to the tubular device with pump effect, on at least one point of the length of said tubular device.

3. Ureteral prosthesis according to claim 1, characterized in that the permanent set distortion is in the shape of at least a single "V".

4. Ureteral prosthesis according to claim 3, characterized in that, where the permanent set distortion is in the form of multiple "V"s, these are arranged on the same side in relation to the axis of the prosthesis.

5. Ureteral prosthesis according to claim 3, characterized in that, where the permanent set distortion is in the form of multiple "V"s, these are arranged on both sides relative to the axis of the prosthesis.

6. Ureteral prosthesis according to claim 1, characterized in that the permanent set distortion is in form of a closed structure with rounded angles.

7. Ureteral prosthesis according to claim 1, characterized in that the permanent set distortion takes the form of a Bellofram type diaphragm.

8. Ureteral prosthesis according to any one of claims 1 to 3, 6 or 7, characterized in that, in addition, it is provided with a second anti-reflux valve incorporated into the length of the tubular device, upstream of the permanent set distortion.

9. Ureteral prosthesis according to any one of claims 1 to 3, 6 or 7, characterized in that said upstream end for implantation into the organism, opposite to the vesical end, includes a rounded edge.

10. Ureteral prosthesis in accordance with claim 9, characterized in that said upstream end presents a shape which determines the formation of apertures for the outflow of urine, even in the event of closure of the upstream end by accidental application thereof against the surrounding walls.

11. Ureteral prosthesis in accordance with claim 10, characterized in that the upstream end terminates in an irregular shape.

12. Ureteral prosthesis according to claim 9, characterized in that it includes at least one notch arranged at the upstream end of its lateral wall.

13. Ureteral prosthesis according to claim 9, characterized in that the upstream end includes at least one lateral orifice arranged on the lateral wall of the prosthesis, in the neighborhood of the upstream end.

14. Ureteral prosthesis according to any one of claims 1 to 3, 6 or 7, characterized in that its anastomosis to the bladder is effected with the aid of a flange of tissue ingrowth fabric, which is arranged obliquely with regard to the axis of the prosthesis.

15. Ureteral prosthesis according to claim 8, wherein said upstream end for implantation into the organism has a rounded edge.

16. Ureteral prosthesis according to claim 11, wherein said irregular shape is in the form of a bevel.

17. Ureteral prosthesis according to claim 11, wherein said irregular shape is in the form of a cone.

18. Ureteral prosthesis according to claim 11, wherein said irregular shape is in the form of a cup.

19. Ureteral prosthesis according to claim 11, and including at least one notch arranged at the upstream end of its lateral wall.

20. Ureteral prosthesis according to claim 10, wherein said shape constitutes at least one lateral orifice arranged on the lateral wall of the prosthesis, in the neighborhood of the upstream end.

* * * * *